US009629739B2

(12) United States Patent
Slazas et al.

(10) Patent No.: US 9,629,739 B2
(45) Date of Patent: Apr. 25, 2017

(54) DISTAL CAPTURE DEVICE FOR A SELF-EXPANDING STENT

(71) Applicants: Robert R. Slazas, Pinecrest, FL (US);
Juan A. Lorenzo, Davie, FL (US)

(72) Inventors: Robert R. Slazas, Pinecrest, FL (US);
Juan A. Lorenzo, Davie, FL (US)

(73) Assignee: DePuy Synthes Products, LLC, Raynham, MA (US)

( * ) Notice: Subject to any disclaimer, the term of this patent is extended or adjusted under 35 U.S.C. 154(b) by 0 days.

(21) Appl. No.: 13/799,437

(22) Filed: Mar. 13, 2013

(65) Prior Publication Data

US 2014/0277357 A1    Sep. 18, 2014

(51) Int. Cl.
*A61F 2/966*    (2013.01)

(52) U.S. Cl.
CPC ...... *A61F 2/966* (2013.01); *A61F 2002/9665* (2013.01); *A61F 2230/0093* (2013.01)

(58) Field of Classification Search
CPC .................................. A61F 2/962; A61F 2/82
USPC ............... 606/108, 191, 193, 194, 195, 198; 623/1.11, 1.12
See application file for complete search history.

(56) References Cited

U.S. PATENT DOCUMENTS

| | | | |
|---|---|---|---|
| 5,234,437 A | 8/1993 | Sepetka | |
| 5,250,071 A | 10/1993 | Palermo | |
| 5,261,916 A | 11/1993 | Engelson | |
| 5,263,964 A | 11/1993 | Purdy | |
| 5,312,415 A | 5/1994 | Palermo | |
| 5,344,426 A | 9/1994 | Lau et al. | |
| 5,380,304 A | 1/1995 | Parker | |
| 5,562,698 A | 10/1996 | Parker | |
| 5,601,600 A | 2/1997 | Ton | |
| 5,700,253 A | 12/1997 | Parker | |
| 5,746,769 A | 5/1998 | Ton et al. | |
| 5,762,615 A | 6/1998 | Weier | |
| 5,788,707 A | 8/1998 | Del Toro et al. | |

(Continued)

FOREIGN PATENT DOCUMENTS

| | | |
|---|---|---|
| CN | 1561240 | 1/2005 |
| CN | 101754727 | 6/2010 |

(Continued)

OTHER PUBLICATIONS

European Search Report for counterpart EP Application 14159061 (Jul. 9, 2014)(7 pages).

(Continued)

*Primary Examiner* — Vy Bui
(74) *Attorney, Agent, or Firm* — Cohen & Hildebrand, PLLC

(57) ABSTRACT

A delivery system including a distal capture device that has a sleeve with a passageway defined axially therethrough and one or more elastically deformable sections. Each of the one or more elastically deformable sections has a free terminating end and an opposite end mounted to the distal end of the sleeve. The elastically deformable sections transition between: (i) a fully expanded state in which the elastically deformable section is distally biased in a direction away from the sleeve; and (ii) a retracted state in which the free terminating end of each of the elastically deformable sections is proximally deflected backwards over itself in a direction toward the proximal end of the sleeve.

15 Claims, 3 Drawing Sheets

(56) References Cited

U.S. PATENT DOCUMENTS

| | | |
|---|---|---|
| 5,800,455 A | 9/1998 | Palermo et al. |
| 5,853,418 A | 12/1998 | Ken et al. |
| 5,925,059 A | 7/1999 | Palermo et al. |
| 5,968,069 A | 10/1999 | Dusbabek et al. |
| 6,063,100 A | 5/2000 | Diaz et al. |
| 6,099,546 A | 8/2000 | Gia |
| 6,113,607 A | 9/2000 | Lau et al. |
| 6,179,857 B1 | 1/2001 | Diaz et al. |
| RE37,117 E | 3/2001 | Palermo |
| 6,612,012 B2 | 9/2003 | Mitelberg et al. |
| 6,673,106 B2 | 1/2004 | Mitelberg et al. |
| 6,818,013 B2 | 11/2004 | Mitelberg et al. |
| 6,833,003 B2 | 12/2004 | Jones et al. |
| 6,866,679 B2 | 3/2005 | Kusleika |
| 6,907,298 B2 | 6/2005 | Smits et al. |
| 6,955,685 B2 | 10/2005 | Escamilla et al. |
| 6,960,227 B2 | 11/2005 | Jones et al. |
| 6,960,228 B2 | 11/2005 | Mitelberg et al. |
| 6,966,892 B2 | 11/2005 | Gandhi et al. |
| 7,001,422 B2 | 2/2006 | Escamilla et al. |
| 7,037,331 B2 | 5/2006 | Mitelberg et al. |
| 7,201,769 B2 | 4/2007 | Jones et al. |
| 7,309,351 B2 | 12/2007 | Escamilla et al. |
| 7,367,987 B2 | 5/2008 | Balgobin et al. |
| 7,371,251 B2 | 5/2008 | Mitelberg et al. |
| 7,371,252 B2 | 5/2008 | Balgobin et al. |
| 7,377,932 B2 | 5/2008 | Mitelberg et al. |
| 7,422,569 B2 | 9/2008 | Wilson et al. |
| 7,572,246 B2 | 8/2009 | Wilson et al. |
| 7,608,058 B2 | 10/2009 | Wilson et al. |
| 7,608,089 B2 | 10/2009 | Wallace et al. |
| 7,780,695 B2 | 8/2010 | Jones et al. |
| 7,794,487 B2 | 9/2010 | Majercak et al. |
| 7,799,052 B2 | 9/2010 | Balgobin et al. |
| 7,811,305 B2 | 10/2010 | Balgobin et al. |
| 7,819,891 B2 | 10/2010 | Balgobin et al. |
| 7,819,892 B2 | 10/2010 | Balgobin et al. |
| 7,901,444 B2 | 3/2011 | Slazas |
| 7,918,872 B2 | 4/2011 | Mitelberg et al. |
| 7,942,898 B2 | 5/2011 | Ewers et al. |
| 7,985,238 B2 | 7/2011 | Balgobin et al. |
| 8,002,789 B2 | 8/2011 | Ramzipoor et al. |
| 8,016,872 B2 | 9/2011 | Parker |
| 8,147,534 B2 | 4/2012 | Berez et al. |
| 8,206,413 B2 | 6/2012 | Jones et al. |
| 8,317,859 B2 | 11/2012 | Snow et al. |
| 8,333,796 B2 | 12/2012 | Tompkins et al. |
| 8,574,260 B2 | 11/2013 | Mitelberg et al. |
| 8,591,566 B2 * | 11/2013 | Newell .................. A61F 2/82 623/1.11 |
| 8,926,650 B2 | 1/2015 | Que et al. |
| 2004/0034363 A1 | 2/2004 | Wilson et al. |
| 2004/0199175 A1 | 10/2004 | Jaeger et al. |
| 2004/0267280 A1 | 12/2004 | Nishide et al. |
| 2005/0043755 A1 | 2/2005 | Wilson et al. |
| 2006/0025802 A1 | 2/2006 | Sowers |
| 2006/0025803 A1 | 2/2006 | Mitelberg et al. |
| 2006/0135986 A1 | 6/2006 | Wallace et al. |
| 2006/0241684 A1 | 10/2006 | Wilson et al. |
| 2006/0241685 A1 | 10/2006 | Wilson et al. |
| 2006/0271086 A1 | 11/2006 | Ramzipoor et al. |
| 2006/0276823 A1 | 12/2006 | Mitelberg et al. |
| 2006/0276824 A1 | 12/2006 | Mitelberg et al. |
| 2006/0276825 A1 | 12/2006 | Mitelberg et al. |
| 2006/0276826 A1 | 12/2006 | Mitelberg et al. |
| 2006/0276827 A1 | 12/2006 | Mitelberg et al. |
| 2006/0276828 A1 | 12/2006 | Balgobin et al. |
| 2006/0276829 A1 | 12/2006 | Balgobin et al. |
| 2006/0276830 A1 | 12/2006 | Balgobin et al. |
| 2006/0276832 A1 | 12/2006 | Balgobin et al. |
| 2006/0276833 A1 | 12/2006 | Balgobin et al. |
| 2006/0276834 A1 | 12/2006 | Balgobin et al. |
| 2007/0005099 A1 | 1/2007 | Jones et al. |
| 2007/0010849 A1 | 1/2007 | Balgobin et al. |
| 2007/0010850 A1 | 1/2007 | Balgobin et al. |
| 2007/0118172 A1 | 5/2007 | Balgobin et al. |
| 2008/0119887 A1 | 5/2008 | Que et al. |
| 2008/0132939 A1 | 6/2008 | Wilson et al. |
| 2008/0133028 A1 | 6/2008 | Wilson et al. |
| 2008/0140111 A1 | 6/2008 | Wilson et al. |
| 2008/0140178 A1 | 6/2008 | Rasmussen et al. |
| 2008/0140219 A1 | 6/2008 | Wilson et al. |
| 2008/0140220 A1 | 6/2008 | Wilson et al. |
| 2008/0147201 A1 | 6/2008 | Wilson et al. |
| 2008/0228215 A1 | 9/2008 | Strauss et al. |
| 2008/0300616 A1 | 12/2008 | Que et al. |
| 2008/0306503 A1 | 12/2008 | Que et al. |
| 2008/0306504 A1 | 12/2008 | Win et al. |
| 2009/0177261 A1 | 7/2009 | Teoh et al. |
| 2009/0292303 A1 | 11/2009 | Wilson et al. |
| 2010/0004675 A1 | 1/2010 | Wilson et al. |
| 2010/0042133 A1 | 2/2010 | Ramzipoor et al. |
| 2010/0160944 A1 | 6/2010 | Teoh et al. |
| 2010/0286723 A1 | 11/2010 | Jones et al. |
| 2011/0060360 A1 | 3/2011 | Mitelberg et al. |
| 2011/0178589 A1 | 7/2011 | Andreas et al. |
| 2011/0270347 A1 | 11/2011 | Frei et al. |
| 2011/0270374 A1 | 11/2011 | Orr et al. |
| 2011/0301702 A1 * | 12/2011 | Rust et al. .................. 623/2.11 |
| 2011/0313443 A1 | 12/2011 | Lorenzo et al. |
| 2012/0209310 A1 | 8/2012 | Chen et al. |
| 2013/0138136 A1 | 5/2013 | Beckham et al. |
| 2013/0261659 A1 | 10/2013 | Lorenzo |
| 2014/0277078 A1 | 9/2014 | Slazas et al. |

FOREIGN PATENT DOCUMENTS

| | | |
|---|---|---|
| CN | 102370532 | 3/2012 |
| CN | 102917669 | 2/2013 |
| EP | 1 813 196 | 8/2007 |
| EP | 2 630 936 | 8/2013 |
| WO | 2013162817 | 10/2013 |

OTHER PUBLICATIONS

Copending, co-owned U.S. Appl. No. 13/802,101, filed Mar. 13, 2013.

European Office Action (counterpart EP App. No. 14 159 061.2), Sep. 24, 2015 (6 pages).

\* cited by examiner

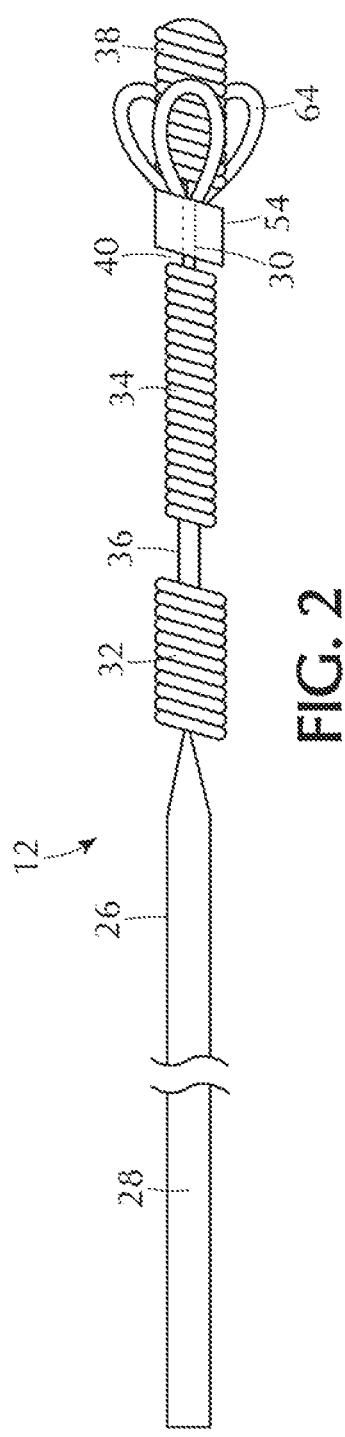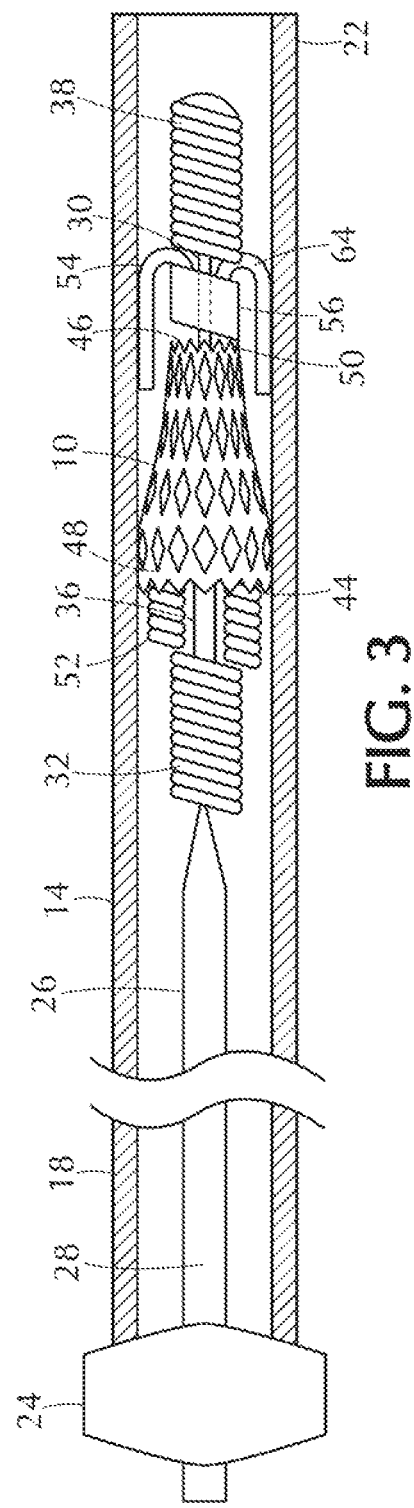

DISTAL CAPTURE DEVICE FOR A SELF-EXPANDING STENT

BACKGROUND OF THE INVENTION

Field of the Invention

The present invention relates to self-expanding intravascular devices for implantation within the vessel of a body. In particular, the present invention relates to an improved distal capture device for use with a self-expanding stent in the treatment of blood vessel disorders.

Description of Related Art

Expandable stents, i.e., expandable tubular skeletal structures, are commonly used today for such treatments as reinforcing diseased blood vessels, opening occluded blood vessels or relieving pressure in aneurysms. Stents that are expandable may be classified as either "balloon expandable" or "self-expanding." Balloon-expandable stents expand upon the inflation of the balloon, whereas self-expanding stents automatically expand upon removal of a force that otherwise retains the stent in an elastically compressed state. Different types of self-expanding stents have been developed, for example, a laser cut stent or a braided stent. A catheter-based delivery system is used to position the expandable stent at a desired location within a blood vessel. Many systems are available for delivering the stent to the desired location. Several exemplary delivery system configurations are disclosed in U.S. Pat. Nos. 7,309,351; 7,201,769; 7,037,331; 7,001,422; 6,960,228; 6,960,227; 6,955,685; 6,833,003; 6,818,013; 6,673,106; 6,612,012, all of which are co-owned by the same assignee of the present invention and each is hereby incorporated by reference in its entirety.

Axial traversal of the stent within the blood vessel occurs using a delivery catheter having a lumen defined axially therethrough for receiving the stent while in a compressed/unexpanded state having a reduced diameter. The catheter is sufficiently flexible, yet rigid, so that it may be pushed distally as it transverses through a blood vessel. While in a compressed state, the stent is introduced into the lumen via the proximal end of the delivery catheter. Conventional self-expanding stents may have a pushing surface to aid in advancing the stent distally through the catheter. Upon emerging out from the distal end of the delivery catheter, the stent automatically deploys to an expanded state in physical contact with the interior surface of the blood vessel.

The distal or leading edge of the expandable stent presses outward against the inner surface of the delivery catheter as it traverses therethrough. Due to its small size and delicate construction, it is desirable to minimize delivery forces required for the stent to transverse axially through the lumen of the catheter. When traversing axially, the distal or leading edge of a self-expanding stent may undesirably radially flare open thereby requiring significant supplemental delivery force to push past any obstacle (e.g., features, edges or imperfections) encountered along the way within the lumen of the delivery catheter. It would therefore be desirable to develop an improved delivery system for a self-expanding stent that eliminates or minimizes supplemental delivery forces required to push the distal leading edge of the stent past any obstacle disposed along the lumen of the delivery catheter.

SUMMARY OF THE INVENTION

One aspect of the present invention is directed to a catheter-based delivery system in which the distal end of the self-expanding stent is constrained radially by plural elastically deformable sections of a distal capture device while in the retracted state proximally deflected thereby eliminating or minimizing the need for supplemental delivery forces required to push the self-expanding stent axially past obstacles disposed within the lumen of the delivery catheter.

Another aspect of the present invention relates to a delivery system including a distal capture device that has a sleeve with a passageway defined axially therethrough and one or more elastically deformable sections. Each of the one or more elastically deformable sections has a free terminating end and an opposite end mounted to the distal end of the sleeve. The elastically deformable sections transition between: (i) a fully expanded state in which the elastically deformable section is distally biased in a direction away from the sleeve; and (ii) a retracted state in which the free terminating end of each of the elastically deformable sections is proximally deflected backwards over itself in a direction toward the proximal end of the sleeve.

Yet another aspect of the present invention is directed to a method for using a delivery system including a distal capture device that has a sleeve with a passageway defined axially therethrough and one or more elastically deformable sections. The delivery system further includes a self-expanding stent having a proximal end and an opposite distal end, wherein the distal end of the stent overlaps with the proximal end of the sleeve of the distal capture device. Each of the one or more elastically deformable sections has a free terminating end and an opposite end mounted to the distal end of the sleeve. The elastically deformable sections transition between: (i) a fully expanded state in which the elastically deformable section is distally biased in a direction away from the sleeve; and (ii) a retracted state in which the free terminating end of each of the elastically deformable sections is proximally deflected backwards over itself in a direction toward the proximal end of the sleeve. The method includes the step of traversing the delivery system axially through a blood vessel to a treatment site therein while simultaneously: (i) maintaining the self-expanding stent in a compressed state; and (ii) maintaining the at least one elastically deformable section of the distal capture device in the retracted state proximally deflected over itself in the direction towards the proximal end of the sleeve constraining the distal end of the self-expanding stent from enlarging radially.

BRIEF DESCRIPTION OF THE DRAWING

The foregoing and other features of the present invention will be more readily apparent from the following detailed description and drawings of illustrative embodiments of the invention wherein like reference numbers refer to similar elements throughout the several views and in which:

FIG. 2 is an enlarged partial cross-sectional view of the present inventive delivery system including the distal capture device in a full-expanded state (distally biased) without the stent;

FIG. 3 is an enlarged partial cross-sectional view of the delivery system including the distal capture device in a retracted state (proximally deflected) covering the distal leading end of a self-expanding stent in a compressed state as the delivery system traverses axially through the blood vessel.

DETAILED DESCRIPTION OF THE INVENTION

Figure 1A:
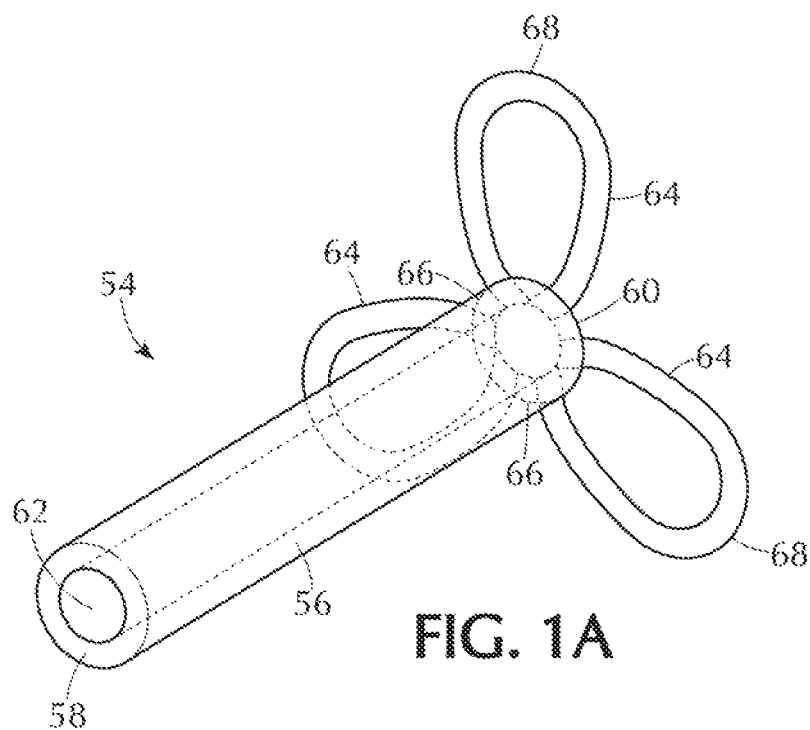
FIG. 1A is an enlarged perspective view of an exemplary embodiment of the distal capture device in accordance with the present invention.
Figure 1B:
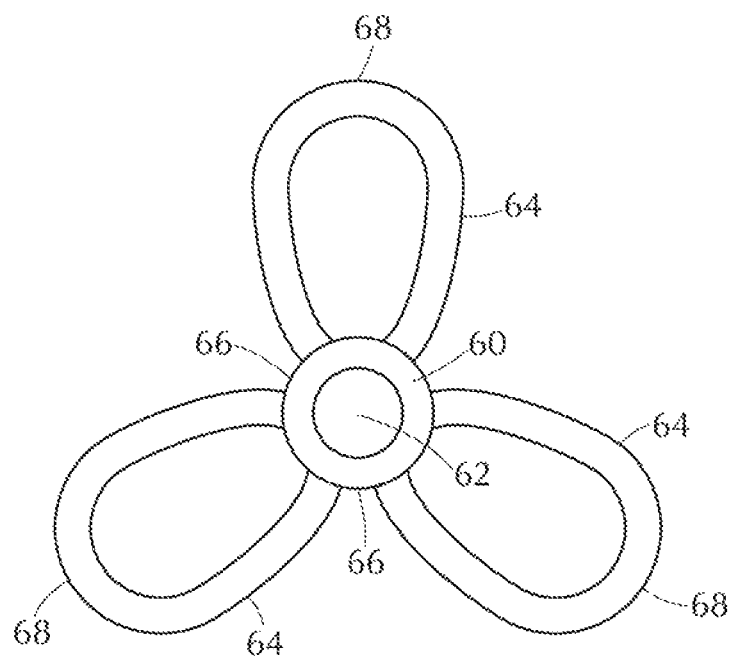
FIG. 1B is an enlarge view of the distal capture device of FIG. 1A from its leading distal end.

The terms "proximal"/"proximally" and "distal"/"distally" refer to a direction closer to or away from, respectively, an operator (e.g., surgeon, physician, nurse, technician, etc.) who would insert the medical device into the patient, with the tip-end (i.e., distal end or leading end) of the device inserted inside a patient's body. Thus, for example, a "proximal direction" would refer to the direction towards the operator, whereas "distal direction" would refer to the direction away from the operator towards the leading or tip-end of the medical device.

The term "stent" refers to a device or structure that provides or is configured to provide rigidity, expansion force, or support to a body pan, for example, a diseased or otherwise compromised body lumen (e.g., blood vessel or coronary arteries).

The term "self-expanding stent" refers to a stent having a reduced diameter configuration when subject to an external constraining force and automatically expanding to an enlarged diameter when the external constraining force is withdrawn.

The present inventive distal capture device is used with a self-expanding stent. Any type of self-expanding stent may be used, for example, a laser cut stent or a braided stent.

FIG. 2 is an enlarged partial cross-sectional view of an exemplary delivery system 12 without the self-expanding stent or delivery catheter. Delivery system 12 includes an elongated core member 26 which is a generally a wire, preferably made of Nitinol, but may also be made from other metal alloys or a polymer material. The core member 26 may be shaped and designed with one or more tapers axially so that proximal section 28 of the core member 26 has a greater diameter than the distal section 30 of the core member 26. Preferably, the diameter of the proximal section 28 of the core member 26 is approximately 0.016 inches while the diameter of the distal section 30 is approximately 0.002 inches. The greater diameter of the proximal section 28 imparts sufficient stiffness to push the core member 26 through the delivery catheter 14, while the smaller diameter of the distal section 30 provides flexibility for the core member 26 to traverse relatively narrow diameter blood vessels.

Delivery system 12 in FIG. 2 further includes a proximal cylindrical member 32 disposed about the distal section 30 of the core member 26. Preferably, the proximal cylindrical member 32 is a helically wound flexible coil with an outside diameter of approximately 0.016 inches. The coil may be made of a polymer material, but the preferred material is metal. An intermediate cylindrical member 34 (about which the stent is mounted) is also disposed about the core member 26 distally from and spaced apart a predetermined distance from the proximal cylindrical member 32 thereby defining a first gap 36. The length of the first gap is preferably in a range from approximately 0.019 inches to approximately 0.19 inches, most preferably a length of approximately 0.040 inches. Intermediate cylindrical member 34 may be a cylindrical sleeve or a coil, having a preferred outer diameter of approximately 0.012 inches. The intermediate cylindrical member 34 may include a radiopaque portion to serve as a marker and preferably formed from a material such as platinum, gold or tantalum. This radiopaque portion is preferably centered with respect to the self-expanding stent and preferably has a length greater than approximately 10 percent of the length of the self-expanding stent.

A distal cylindrical member 38 is also disposed about the core member 26 distally from and spaced apart from the intermediate cylindrical member 34 defining therebetween a second gap 40. A preferred length of the second gap 40 may range from approximately 0.019 inches to approximately 0.19 inches, most preferably a length of approximately 0.040 inches. Preferably, the distal cylindrical member 38 is a helically wound flexible coil with an outside diameter of approximately 0.016 inches. The coil may be made of a polymer material, but once again the preferred material is metal. Distal cylindrical member 38 may also be shapeable so that the core member 26 may be used as a guidewire. For example, the distal cylindrical member 38 may be slightly angled to permit the core member 26 to easily navigate through the vasculature of the body.

Referring to FIG. 3, the delivery system 12 further includes a delivery catheter 14 (an elongated tube) with a lumen 16 defined axially therethrough. The lumen 16 of the delivery catheter 14 preferably has a diameter in the range of approximately 0.010 inches to approximately 0.25 inches, most preferably having a diameter of approximately 0.021 inches. Preferably, a proximal section 18 of the delivery catheter 14 is formed of a nylon material having a durometer in a range of approximately 60 D to approximately 75 D. Proximal section 18 is sufficiently flexible to traverse a blood vessel, yet sufficiently rigid so that it may be pushed distally through a blood vessel. An opposite distal or leading section 22 of the delivery catheter 14 is preferably formed of a pellethane material having a durometer of between approximately 25 D and approximately 55 D, most preferably having a durometer of approximately 40 D.

To aid in insertion of the delivery catheter 14 into a blood vessel, delivery system 12 preferably includes a winged hub 24 coupled to the proximal section 18 of the delivery catheter 14. Winged hub 24 is preferably made from plastic and configured to be slideably disposed within the lumen 16 of the delivery catheter 14.

A self-expanding stent 10 is mounted on the intermediate cylindrical member 34. Any type of pattern or configuration for the self-expanding stent 10 is contemplated and within the scope of the present invention. Examples of such stents are disclosed in U.S. Pat. No. 6,673,106, issued on Jan. 6, 2004, entitled "Intravascular Stent Device" and in U.S. Pat. No. 6,818,013, issued on Nov. 16, 2004, entitled "Intravascular Stent Device", each of which is herein incorporated by reference in its entirety. Self-expanding stent 10 is preferably laser cut from a tubular piece of Nitinol and thereafter treated so as to exhibit superelastic properties at body temperature. The self-expanding stent 10 may include proximal and distal legs 44 and 46 that are attached to the respective proximal and distal ends 48 and 50 of the stent 10 and extend along the longitudinal axis of the stent 10. In addition, the self-expanding stent 10 includes anchor members 52 which may be attached to the proximal end 48 of the stent 10, the proximal legs 44 of the stent 10 and/or at any location along the stent between ends 48 and 50. Anchor members 52 may be projections made from polymer or metallic material which extend generally parallel to the longitudinal axis the stent 10 and extend downward toward the longitudinal axis of the stent 10.

Preferably, the anchor members 52 are helically wound flexible coils made of a radiopaque material for use during fluoroscopic visualization. As the self-expanding stent 10 is positioned and mounted on the intermediate cylindrical member 34, anchor members 52 attached to the proximal end 48 or proximal legs 44 of the stent 10 align with and are disposed within the first gap 36. The proximal end of the self-expanding stent 10 is secured in place by anchor members 52 while its opposite distal end by a distal capture device 54. The self-expanding stent 10 is thus able to be pushed and pulled through the delivery catheter 14 without damaging or deforming the stent 10. Without being secured to the stent 10 in any way (e.g., via wires or sutures), the distal capture device 54 in accordance with the present invention is disposed to constrain radially the distal leading end 46 of stent 10 from flaring open when traversing axially through the lumen 16 of the delivery catheter 14. Distal capture device 54 is slidably disposed along core member 26 within the second gap 40 between the distal cylindrical member 38 and the intermediate cylindrical member 34.

Referring to FIG. 1A, the present inventive distal capture device 54 comprises a sleeve 56 having a proximal end 58, a distal end 60 and a passageway 62 defined axially therethrough. Passageway 62 has a diameter sufficiently large to allow core member 26 to slidably pass therethrough. An outer diameter of the sleeve 56 is smaller than the opening 8 defined axially through stent 10. Accordingly, when the self-expanding stent 10 is loaded into the delivery catheter 14 only a portion of the proximal end 58 of sleeve 56 is inserted, starting from the distal leading end 50 of the stent 10, into its opening 8, as depicted in FIG. 3.

The distal capture device 54 also includes a plurality of elastically deformable sections 64 that together represent a distal leaf component. In accordance with the present invention, the distal capture device 54 may be a single integral piece made of a single material (e.g., Nitinol or spring steel). Alternatively, the sleeve 56 may simply be a weld type feature instead of a discrete piece of material. It is also contemplated that the distal capture device 54 be two or more pieces (e.g., a sleeve made of any material suitable for joining and/or holding the plural elastically deformable sections 64 in a distally biased position (e.g., platinum, stainless steel or polyimide) and a distal leaf component preferably made of Nitinol or spring steel). Either configuration may be secured in any way to the core such as, but not limited to, welding, crimping, soldering or an adhesive bond. In yet another configuration, the sleeve 56 may secure the distal leaf component to the core by mounting over a portion of the distal leaf component.

Each elastically deformable section 64 has a free terminating end 68 and an opposite proximal end 66 that is affixed, attached, mounted, connected or otherwise secured to the distal end 60 of sleeve 56. In the exemplary embodiment illustrated in the figures, the elastically deformable sections 64 are closed loops made of an elastically deformable material such as Nitinol or any other material (e.g., metal or polymer) that does not plastically deform/exceed its yield strength when in the proximally biased position. Other configurations may be utilized instead of a loop, such as a flap. Despite three elastically deformable sections 64 being shown, the present invention may be modified to include any number of one or more elastically deformable sections.

Figure 4:
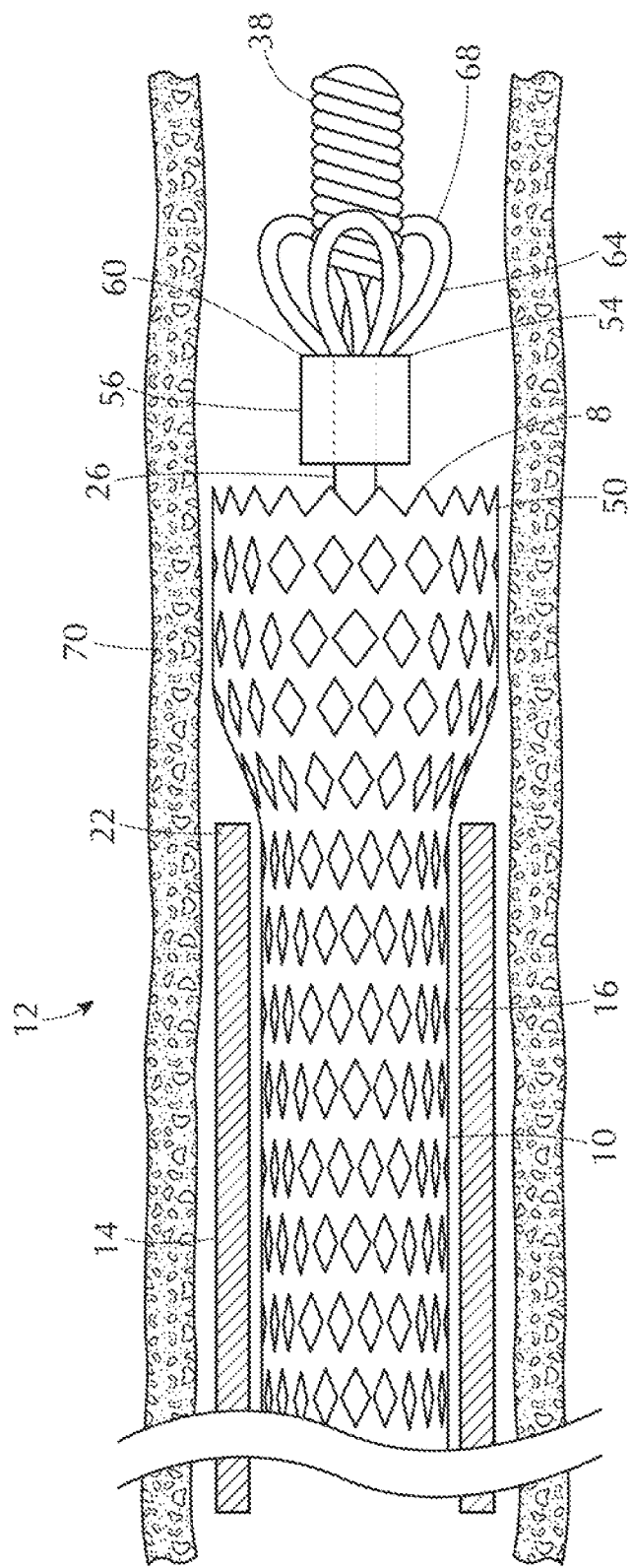
FIG. 4 is an enlarged partial cross-sectional view of the present inventive delivery system including the distal capture device in a fully expanded state (distally biased) with the distal end of the self-expanding stent in an expanded state deployed at its desired location within the blood vessel.

Each elastically deformable section 64 is adaptable between two states. While in a fully expanded state, free from any external retractive force, the elastically deformable sections 64 are distally biased in a direction away from sleeve 56 so that its free terminating ends 68 are at least substantially aligned with, if not extend beyond, the distal end 60 of the sleeve 56, as illustrated in FIG. 2. Upon the free terminating ends 68 being subject to an external retractive force, each elastically deformable section 64 is bendable onto itself to a retracted state in which its associated free terminating ends 68 are proximally deflected (i.e., deflected toward the proximal end 58 of sleeve 56), as shown in FIG. 3. Specifically, the external retractive force (in a proximal direction toward the proximal end 58 of the sleeve 56) is applied to its free terminating end 68 until at least a portion of each elastically deformable section 64 is bent backwards onto itself. Preferably, the external retractive force is applied at least until the free terminating end 68 of each of the elastically deformable sections 64 are substantially aligned with or extend in a proximal direction past the distal end 60 of the sleeve 56. When loaded into the delivery catheter 14, the plural elastically deformable sections 64 while in the retracted state are prevented from reverting or transitioning back to a fully expanded state by the interior walls of the lumen 16 with which they are physically in contact (as shown in FIG. 3). Upon withdrawing the delivery catheter 14 in a proximal direction until its distal end 22 is clear of the free terminating ends 68, the elastically deformable sections 64 automatically revert or transition from the retracted state (the elastically deformable sections proximally deflected) to the fully expanded state (the elastically deformable sections distally biased). As illustrated in FIG. 4, while the distal capture device 54 is in a fully expanded state (with the elastically deformable sections distally biased), the distal leading end of the self-expanding stent 10 is allowed to expand radially outward until physical contacting the inner wall of the blood vessel. Once deployed, the self-expanding stent 10 may be anchored or secured in place at the desired location within the blood vessel. In its fully expanded state, the maximum outer diameter of all the elastically deformable sections 46 together is smaller than the diameter of the axial opening 8 defined in the self-expanding stent 10 so that the core member 26 and distal capture device 54, while in a fully expanded state, may be proximally withdrawn from the lumen 16 of the delivery catheter 14 leaving the expanded stent in place within the blood vessel.

During manufacture of the exemplary delivery system 12 illustrated in FIG. 2, distal capture device 54 is disposed about core member 26 within the second gap 40 between the intermediate cylindrical member 34 and the distal cylindrical section 38 with the proximal end 58 of the sleeve 56 proximate the intermediate cylindrical member 34. Stent 10, while in a fully expanded state, is slidable along the core member 26 via the axial opening 8. In the exemplary delivery system 12 shown in FIG. 3, the stent 10 is slid along the core member 26 until substantially aligned with the intermediate cylindrical member 34 and the distal leading end of the stent 10 overlaps in an axial direction only a portion of the proximal end 58 of the sleeve 56 of the distal capture device 54. An external force (axially and/or radially) is applied to stent 10 causing it to transition from a fully expanded state to a compressed state, having a reduced diameter relative to that of the fully expanded state. The stent 10 is interlocked axially along the core member 26 at its distal leading end by the distal capture device 54, while its opposite proximal end is constrained by anchor members 52.

The free terminating ends 68 of the elastically deformable sections 64 are bent backwards/retracted in a proximal direction onto themselves (e.g., proximally deflected) overlapping with the distal end of the stent 10 and radially constrained. One way to accomplish this is by pushing the elastically deformable sections 64 through a tapered tube to bias them proximally and simultaneously radially constrain them. Other methods are contemplated to proximally bias and radially constrain the elastically deformable sections 64 somewhat, if not completely, from flaring open. Preferably, while the elastically deformable sections 64 are in this retracted state: (i) the free terminating ends 68 extend in a proximal direction so as to be at least substantially aligned with, if not beyond, the distal end 60 of the sleeve 56; and (ii) the retracted elastically deformable sections 64 all together define a diameter sufficiently small to be received within the lumen 16 of deployment catheter 14. In this retracted state (with the free terminating ends 68 deflected proximally) the distal capture device 54 constrains radially the distal end of the stent 10 prohibiting or minimizing the degree to which the distal end of the stent is able to radially flare open when traversing axially through the lumen 16 of the delivery catheter 14. Core member 26 with the stent 10 maintained in a compressed state and the elastically deformable sections 64 in a retracted state (proximally deflected) is then introduced via the proximal end 18 of the delivery catheter 14 into the lumen 16.

Once installed in the deployment catheter 14, the plural elastically deformable sections 64 are in physically contact with the interior walls of the lumen 16 of the deployment catheter 14 thereby retaining them in the retracted state (proximally deflected). The loaded delivery system in accordance with the present invention is then inserted into and traverses axially through the blood vessel to a position proximate the treatment site. As is clearly illustrated in FIG. 3, when loaded into the delivery catheter 14 the distal leading end of the stent 10 remains constrained, captured or covered by the plural elastically deformable sections 64 (in a retracted state) thereby minimizing, if not preventing all together, the distal end of the stent 10 from radially flaring open. Accordingly, the distal capture device minimizes, if not eliminates, the need for supplemental delivery forces to advance the stent axially over any obstacles disposed in the lumen 16 of the deployment catheter 14.

Once positioned at the desired location in the blood vessel, while the core member 26 remains in place, the delivery catheter 14 is partially withdrawn in a proximal direction until the free terminating ends 68 of the elastically deformable sections 64 are clear of the deployment catheter 14 (i.e., free terminating end 68 are no longer physically constrained by the interior walls of the lumen 16 of the deployment catheter 14). As soon as the free terminating ends 68 are no longer constrained by the interior surface of the lumen 16 of the delivery catheter 14, elastically deformable sections 64 automatically revert back to their fully expanded state (distally biased) and, in turn, the distal portion of the stent 10 automatically expands until physically contacting the interior wall of the blood vessel 70, as depicted in FIG. 4. Delivery catheter 14 is again moved further in a proximal direction until the proximal portion of the stent expands and allows the anchor members 52 to become released. Stent 10 is now fully deployed. While the deployed stent 10 remains in place, core member 26 together with the distal capture device 54 in a fully expanded state (distally biased) may be proximally withdrawn from the blood vessel.

The present inventive distal capture/release device in accordance with the present invention is relatively inexpensive to manufacture, suitable for use with conventional self-expanding stent delivery systems without having to alter its design, and extremely reliable.

In accordance with the present invention, the distal end of the self-expanding stent is constrained radially by the plural elastically deformable sections of the distal capture device while in the retracted state thereby minimizing, if not eliminating, the need for supplemental delivery forces required to push the self-expanding stent axially past obstacles disposed within the lumen of the delivery catheter.

Thus, while there have been shown, described, and pointed out fundamental novel features of the invention as applied to a preferred embodiment thereof, it will be understood that various omissions, substitutions, and changes in the form and details of the devices illustrated, and in their operation, may be made by those skilled in the art without departing from the spirit and scope of the invention. For example, it is expressly intended that all combinations of those elements and/or steps that perform substantially the same function, in substantially the same way, to achieve the same results be within the scope of the invention. Substitutions of elements from one described embodiment to another are also fully intended and contemplated. It is also to be understood that the drawings are not necessarily drawn to scale, but that they are merely conceptual in nature. It is the intention, therefore, to be limited only as indicated by the scope of the claims appended hereto.

Every issued patent, pending patent application, publication, journal article, book or any other reference cited herein is each incorporated by reference in their entirety.

What is claimed is:

1. A delivery system comprising:
   a distal capture device comprising:
       a sleeve having a proximal end, an opposite distal end and a passageway defined longitudinally therethrough;
       at least one elastically deformable section, each of the at least one elastically deformable section has a free terminating end and an opposite end mounted to the distal end of the sleeve; wherein the at least one elastically deformable section transitions between: (i) a fully expanded state in which the at least one elastically deformable section is distally biased in a longitudinal direction of the sleeve away from the sleeve; and (ii) a retracted state in which the free terminating, end of each of the at least one elastically deformable section is proximally deflected backwards over itself in a direction toward the proximal end of the sleeve;
   a self-expanding stent having, a proximal end and an opposite distal end; the distal end of the stem overlapping with the proximal end of the sleeve of the distal capture device; and
   a core member slidably receivable within the passageway of the sleeve of the distal capture device;
   wherein irrespective of the state of the elastically deformable section the distal capture device is not secured to the stent.

2. The delivery system in accordance with claim 1, further comprising a delivery catheter having a proximal end, an opposite distal end and a lumen defined axially therethrough for receiving the distal capture device and the core member.

3. The delivery system in accordance with claim 1, wherein the distal capture device has a plurality of elastically deformable sections.

4. The delivery system in accordance with claim 3, wherein the distal capture device has three elastically deformable sections.

5. The delivery system in accordance with claim 1, wherein the at least: one elastically deformable section of the distal capture device is in the fully expanded state distally biased when not subject to any external retractive force in a direction towards the proximal end of the sleeve.

6. The delivery system in accordance with claim 1, wherein the at least one elastically deformable section of the distal capture device is in the retracted state proximally deflected when its free terminating end is subject to an external retractive force in a direction towards the proximal end of the sleeve.

7. The delivery system in accordance with claim 1, wherein the at least one elastically deformable section transitions from the fully expanded state to the retracted state only when the free terminating end is subject to an external retractive three in a direction towards the proximal end of the sleeve.

8. The delivery system in accordance with claim 1, wherein an outer diameter of the sleeve is smaller than an opening defined axially through the self-expanding stent.

9. The delivery system in accordance with claim 1, wherein the at least one elastic deformable section is a loop or a flap.

10. The delivery system in accordance with claim 1, wherein in the fully expanded state, the free terminating end of the at least one elastically deformable section extends in a longitudinal direction of the sleeve beyond the distal end of the sleeve.

11. A method for using a delivery system, wherein the delivery system includes: a distal capture device comprising: a sleeve having a proximal end, an opposite distal end and a passageway defined longitudinally therethrough; at least one elastically deformable section, each of the at least one elastically deformable section has a free terminating end and an opposite end mounted to the distal end of the sleeve; wherein the at least one elastically deformable section transitions between: (i) a fully expanded state in which the at least one elastically deformable section is distally biased in a longitudinal direction of the sleeve away from the sleeve; and (ii) a retracted state in which the free terminating end of each of the at least one elastically deformable section is proximally deflected backwards over itself in a direction toward the proximal end of the sleeve; a core member slidably receivable within the passageway of the sleeve of the distal capture device; a delivery catheter having a proximal end, an opposite distal end and a lumen defined axially therethrough for receiving the distal capture device and the core member; a self-expanding stent having a proximal end and an opposite distal end; the distal end of the stem overlapping with the proximal end of the sleeve of the distal capture device, wherein irrespective of the state of the elastically deformable section the distal capture device is not secured to the stent, the method comprising the step of:

traversing the delivery system axially through a blood vessel to a treatment site therein while simultaneously: (i) maintaining the self-expanding stent in a compressed state; and (ii) maintaining the at least one elastically deformable section of the distal capture device in the retracted state proximally deflected over itself in the direction towards the proximal end of the sleeve constraining the distal end of the self-expanding stem from enlarging radially.

12. The method in accordance with claim 11, further comprising the step of:

while the core member, the distal capture device and the self-expanding stent remain in place within the blood vessel, partially withdrawing in a proximal direction from the blood vessel the delivery catheter until its distal end clears the free terminating end of the at least one elastically deformable section causing automatically: (i) the at least one elastically deformable section to return to its fully expanded state biased distally in a direction away from the sleeve; and (ii) the distal end of the self-expanding stent to expand radially until physically contacting interior walls of the blood vessel.

13. The method in accordance with claim 11, wherein in the fully expanded state the at least one elastically deformable section doesn't physically contact the interior walls of the blood vessel or the self-expanding stem.

14. The method in accordance with claim 11, further comprising the steps of:

fully withdrawing in the proximal direction the delivery catheter from the blood vessel; and while maintaining the self-expanding stem in an expanded state in place within the blood vessel, fully withdrawing in the proximal direction simultaneously the core member and the distal capture device disposed thereon by sliding them through an axial opening defined in the self-expanding stem.

15. The method in accordance with claim 11, wherein in the fully expanded state, the free terminating end of the at least one elastically deformable section extends in a longitudinal direction of the sleeve beyond the distal end of the sleeve.

* * * * *

UNITED STATES PATENT AND TRADEMARK OFFICE
CERTIFICATE OF CORRECTION

PATENT NO. : 9,629,739 B2
APPLICATION NO. : 13/799437
DATED : April 25, 2017
INVENTOR(S) : Slazas et al.

It is certified that error appears in the above-identified patent and that said Letters Patent is hereby corrected as shown below:

In the Claims

Column 8, Claim 1, Line 45, delete the ",".
Column 8, Claim 1, Line 49, delete the ",".
Column 8, Claim 1, Line 50, change "stem" to --stent--.
Column 9, Claim 5, Line 2, delete the ":".
Column 9, Claim 7, Line 16, change "three" to --force--.
Column 10, Claim 11, Line 2, change "stem" to --stent--.
Column 10, Claim 11, Line 14, change "stem" to --stent--.
Column 10, Claim 13, Line 31, change "stem" to --stent--.
Column 10, Claim 14, Line 36, change "stem" to --stent--.
Column 10, Claim 14, Line 41, change "stem" to --stent--.

Signed and Sealed this
First Day of August, 2017

Joseph Matal
*Performing the Functions and Duties of the*
*Under Secretary of Commerce for Intellectual Property and*
*Director of the United States Patent and Trademark Office*